(12) United States Patent
Webler et al.

(10) Patent No.: US 6,974,557 B1
(45) Date of Patent: Dec. 13, 2005

(54) METHODS FOR FORMING AN OPTICAL WINDOW FOR AN INTRACORPOREAL DEVICE AND FOR JOINING PARTS

(75) Inventors: William E. Webler, Escondido, CA (US); Michael D. Whitt, Carlsbad, CA (US); Marc M. Jalisi, Weston, FL (US); Andrej M. Chudy, Temecula, CA (US); Kevin M. Phillips, Temecula, CA (US); Marc L. Speck, Temecula, CA (US)

(73) Assignee: Advanced Cardiovasculer Systems, Inc., Santa Clara, CA (US)

( * ) Notice: Subject to any disclaimer, the term of this patent is extended or adjusted under 35 U.S.C. 154(b) by 579 days.

(21) Appl. No.: 10/025,334

(22) Filed: Dec. 18, 2001

(51) Int. Cl.$^7$ .................... B29C 35/08; B29C 35/12; B29C 43/18
(52) U.S. Cl. .................... 264/443; 264/486; 264/492; 264/496; 264/261; 264/263; 264/267; 264/277; 264/278; 264/320
(58) Field of Search .................... 264/443, 486, 264/492, 493, 496, 69, 249, 261, 263, 265, 264/267, 275, 277, 278, 319, 320

(56) References Cited

U.S. PATENT DOCUMENTS

| | | | | |
|---|---|---|---|---|
| 4,213,536 A | * | 7/1980 | Hafner | 220/663 |
| 5,017,259 A | * | 5/1991 | Kohsai | 156/294 |
| 5,160,559 A | * | 11/1992 | Scovil et al. | 156/73.6 |
| 5,321,501 A | | 6/1994 | Swanson et al. | 356/345 |
| 5,459,570 A | | 10/1995 | Swanson et al. | 356/345 |
| 5,514,115 A | * | 5/1996 | Frantzen et al. | 604/531 |
| 5,776,114 A | * | 7/1998 | Frantzen et al. | 604/531 |
| 5,811,043 A | * | 9/1998 | Horrigan et al. | 264/138 |
| 5,935,075 A | | 8/1999 | Casscells et al. | 600/474 |
| 5,948,184 A | * | 9/1999 | Frantzen et al. | 148/563 |
| 5,951,929 A | * | 9/1999 | Wilson | 264/139 |
| 6,063,318 A | * | 5/2000 | Houser et al. | 264/248 |
| 6,103,037 A | * | 8/2000 | Wilson | 156/158 |
| 6,111,645 A | | 8/2000 | Tearney et al. | 356/354 |
| 6,134,003 A | | 10/2000 | Tearney et al. | 356/345 |
| 6,375,774 B1 | * | 4/2002 | Lunn et al. | 156/158 |
| 6,548,010 B1 | * | 4/2003 | Stivland et al. | 264/482 |
| 6,797,217 B2 | * | 9/2004 | McCrea et al. | 264/229 |

OTHER PUBLICATIONS

Brezinski et al., "Optical Coherence Tomography for Optical Biopsy" Circulation 93(6):1206-1213 (Mar. 1996).

(Continued)

*Primary Examiner*—Angela Ortiz
(74) *Attorney, Agent, or Firm*—Fulwider Patton Lee & Utecht, LLP

(57) ABSTRACT

Optical windows for intracorporeal devices, intracorporeal devices comprising a window and a method for forming a window for an intracorporeal device are provided. The method comprises placing within a mold an assembly comprising a mandrel located within a pair of parts separated by a collar of window material, heating the window preform effective to cause the window material to soften, and applying force to urge together the pair of parts to deform the window material so as to form a window. The intracorporeal devices, such as imaging devices, include guidewires, catheters, endoscopes. In addition, the method is suitable for joining plastic parts to other parts, such as metal and ceramic parts.

21 Claims, 4 Drawing Sheets

OTHER PUBLICATIONS

Brezinski et al., "Assessing atherosclerotic plaque morphology: comparison of optical coherence tomography and high frequency intravascular ultrasound" Heart 77:397-403 (1997).

Brezinski et al., "Optical Biopsy with Optical Coherence Tomography: Feasibility for Surgical Diagnostics" Journal of Surgical Research 71:32-40 (1997).

Fujimoto et al., "New Technology for High-Speed and High-Resolution Optical Coherence Tomography" Annals New York Academy of Sciences 95-107.

Tearney et al., "Scanning single-mode fiber optic catheter-endoscope for optical coherence tomography" Optics Letters 21(7):543-545 (Apr. 1996).

* cited by examiner

METHODS FOR FORMING AN OPTICAL WINDOW FOR AN INTRACORPOREAL DEVICE AND FOR JOINING PARTS

FIELD OF THE INVENTION

The present invention relates generally to methods and apparatus for manufacturing an optical window for an intracorporeal device that provides functional access to a body lumen, and to methods for joining parts together. In particular, the invention is directed to methods and apparatus for making an optical window for an imaging guidewire, catheter, or endoscope.

BACKGROUND OF THE INVENTION

Intracorporeal devices are devices suitable for introduction into a patient's body, for example, into a body lumen of a patient. Many clinical procedures require the insertion of wires, tubes, probes or other objects into a body lumen of a patient. For example, guidewires and catheters may be used for gaining access to the coronary vasculature, as in an angiogram or in angioplasty. A guidewire is a thin, flexible device used to provide a guiding rail to a desired location within the vasculature (or other body cavity) of a patient. A balloon catheter is a device with an interior lumen with at least a portion of the catheter being able to expand. In coronary angioplasty, a balloon catheter, guided by a guidewire, is positioned within a partially-occluded coronary artery where its balloon portion is expanded in order to press against and enlarge the lumen of a blood vessel in which it is situated. Alternatively, endoscopy requires the introduction of an endoscope into the lumen of a patient, as may be done during a colonoscopy.

The ability to decide where to locate a catheter during a clinical procedure can be improved by providing interior images of the body lumen, such as the blood vessels during angioplasty or the colon during colonoscopy. It is often critical to the success of an angioplasty procedure that a balloon catheter be properly located within a blood vessel. Thus; imaging by guidewire, catheter, or other such device can be of great importance to the success of the procedure.

Imaging endoscopes, guidewires and catheters have been described, as in U.S. Pat. Nos. 5,321,501 and 5,459,570 to Swanson et al., and U.S. Pat. No. 6,134,003 to Tearney et al. Catheters adapted for optical imaging using non-visible light may be useful as well, as disclosed in U.S. Pat. No. 5,935,075 to Cassells et al. Such imaging devices typically use an optical fiber to carry light. All patents, supra and infra, are hereby incorporated by reference in their entirety.

It is often advantageous to have a window in an imaging catheter, imaging guidewire, endoscope, or other imaging probe to allow optical access between the exterior of the device and the optical fiber or light path within the device. U.S. Pat. No. 6,134,003 to Tearney et al. discloses a rigid plastic clear window, or using three or more metal or plastic metering rods to connect two parts of a guidewire across a window. However, the choice of material and the method of construction of the window is critical to the success of the device. A window made of brittle material may break and shatter if it fails, leading to the dispersion of broken window shards within a body lumen if such failure occurs during a clinical procedure. Such materials are thus unacceptable in devices designed for use within a body lumen. A non-brittle, plastic material does not have the disadvantages of a brittle window material.

However, a suitable connection between the window material and other components of an intracorporeal imaging device is required. For use in an intracorporeal imaging device such as a guidewire, catheter, or endoscope, the window must be attached to proximal and distal portions of the intracorporeal imaging device.

Conventional techniques for forming and attaching windows have been found to be difficult and unsuccessful. Use of rods to connect two parts of a guidewire or other intracorporeal imaging device across a window blocks visual access and interferes with the imaging function of a window. The extremely small dimensions of the window components makes conventional molding, extrusion molding, injection molding and insert molding processes difficult and costly to use in making a window for these intracorporeal devices, and such methods only provide a low likelihood of success.

For example, the small outer diameter of a guidewire makes it extremely difficult to use conventional methods to successfully press fit an extruded window over the formed guidewire mating ends. Conventional attempts to expand or drill out the inner diameter of the window tubing to obtain a fit present problems with alignment, obtaining tooling and maintaining low enough tolerances to make a good bond of either desired type. Further, if one were to use conventional techniques and to expand the extruded window to allow a fit over the ends of the guidewire, some window material would assume a larger than desired outer diameter, which would have to be cleanly removed by some other operation. Additionally, the tolerances associated with extrusion (typically +/−0.001") would require that the average cross-sectional area of the window wall be significantly lower than the maximum cross-section possible within its dimensional constraints, so that, with prior art methods, the strength and utility of the window could be impaired.

Conventional methods for bonding the ends of the window with an adhesive so as to mate appropriately with the proximal and distal portions of a guidewire or catheter suffer from similar disadvantages as other conventional methods. Conventional molding processes force a melted plastic into a mold cavity where it rapidly cools. In order to form a tubular window a mold pin must be placed inside the mold to leave a hollow interior. However, with such conventional techniques, while forcing melted plastic into a mold, at least a portion of the melted plastic would cool significantly while flowing into the mold. Conventional techniques would then require that the plastic be forced very rapidly into the cavity under high pressures to fill the cavity before cooling in an attempt to avoid this problem. However, such rapid, high pressure flow would damage or warp the mold pin forming the inner diameter of the window. This is due to the length of the window inner diameter that is required to ensure that the fiber optic assembly can be reliably aligned such that the light exits the window in all bend, temperature and assembly conditions.

Attempting to balance the molding forces by having more than one plastic entrance into the mold requires a more complex and expensive mold. This method suffers from disadvantages due to the low volume of plastic in the window, and the uncertainty involved in timing the plastic flow's entry into the cavity. Additionally, molds and equipment of this type are very expensive.

Accordingly, there is need in the art for methods for forming a window for an imaging guidewire, catheter or endoscope.

SUMMARY

The present invention is directed to methods for forming windows and for joining materials. In some embodiments, the invention is directed to methods for forming a window for an intracorporeal device, windows formed by the novel methods, and intracorporeal devices comprising a window formed by the methods. The novel methods may be used to form optical windows for guidewires, catheters, endoscopes, and other intracorporeal devices useful for accessing a body lumen. For example, the optical window formed by the methods of the invention may comprise a smooth translucent or transparent tube comprising a portion of an imaging guidewire. The methods can be used to form or mold into place very small plastic parts, especially those that require tight tolerances and a small inner diameter of a relatively long length. Thus, in some embodiments, the methods of the invention are effective to join plastic parts, in particular very small plastic parts, with other parts, such as metal or ceramic parts, to form joints and junctions. Devices and methods utilizing the methods of the present invention are disclosed in co-owned applications Ser. No. XXX, "Optical Guidewire Having Windows or Apertures" to Jalisi et al., application Ser. No. YYY "Rotatable Ferrules and Interfaces for Use with an Optical Guidewire," to Webler et al., and application Ser. No. ZZZ "Sheath for Guiding Imaging Instruments," to Webler et al., all of which are filed concurrently herewith, and the disclosures of which are all hereby incorporated by reference in their entirety.

An optical window formed by the methods of the invention may include a smooth translucent or transparent tube that is attached to distal and proximal portions of an imaging guidewire, an imaging catheter, an imaging endoscope, or other device suitable for accessing a body lumen. By way of example, the methods will be illustrated with a description of the formation of a window for an imaging guidewire. However, it will be understood that the methods may also be used to form windows for catheters, endoscopes, and any other intracorporeal device useful for accessing a body lumen.

The invention includes methods for forming a window for an intracorporeal device, comprising placing an assembly with a window preform at least partially within a mold, softening the window preform, and applying force. In some embodiments, softening the window preform may be accomplished by heating the window preform. The assembly includes a proximal tubular member, a distal member, a window preform, and a mandrel. A window preform is disposed between the proximal tubular member and the distal member. A window preform may flow when desired, and may be made, at least in part, of a material that softens when its temperature is raised. The softened window preform material may be deformed onto proximal and distal portions of an intracorporeal device, which portions may be configured so as to contact, engage or grip the window perform or formed window. The assembly has a longitudinal axis, and the mandrel is disposed along the longitudinal axis at least partially within the proximal tubular member, the window preform, and the distal member. The step of raising the temperature of the window preform may be effective to soften the window preform. The step of applying force is effective to urge together the proximal tubular member and the distal member, and is effective to deform the window preform so as to form a window or to join separate parts together. In other embodiments, the window preform is made, at least in part, of a material that hardens upon warming, exposure to light, or other treatment.

Heating the window preform may be effected, for example, by at least one method selected from the group consisting of induction heating, conduction heating, infrared radiation, ultrasonic heating, friction heating, hot air heating, and allowing the preform temperature to rise to ambient temperature.

In some embodiments of the methods for forming a window for an intracorporeal device, the mandrel protrudes from an end of the assembly, or, in further embodiments of the methods, the mandrel protrudes from each end of the assembly. The mandrel may have a polished distal end, may be coated with a coating such as a lubricious coating, lined with a lining such as a lubricious lining, and may be polished and/or treated, for example, to have a smooth or a lubricious surface. Any lubricious coating, such as a coating of a fluoropolymer (e.g., Teflon®), titanium nitride, or other coating known in the art, may be used in the practice of the novel methods.

The invention also provides methods for joining a plastic part with a tubular member. Such methods include placing at least partially within a mold an assembly comprising a tubular member, a mandrel and a plastic preform that softens when heated; softening the plastic preform; and applying force effective to urge together the tubular member and the plastic preform effective to deform the plastic preform and to join the plastic preform to the tubular member. In some embodiments, the plastic preform may be softened by heating.

The mold may be comprised of a suitable material or combination of materials having a higher melt temperature than the window material, such as metal, plastic, ceramic, glass, and combinations of these materials. In some embodiments of the methods, the mold comprises borosilicate glass. The mold may be coated on one or more surfaces with a coating such as a lubricious coating, lined on one or more surfaces with a lining such as a lubricious lining, and may be polished and/or treated on one or more surfaces, for example, to have a smooth or a lubricious surface. Any lubricious coating may be used in the practice of the novel methods.

Optical radiation may be useful in imaging and optical sensing. Window materials comprise translucent materials (i.e., materials capable of transmitting optical radiation such as light), including materials which may be transparent (i.e., translucent materials capable of transmitting an image). The terms "light" and "optical radiation" are used herein to mean electromagnetic radiation including but not limited to visible light, infrared radiation, ultraviolet radiation, and other radiation. Optical radiation may include radiation having a wavelength in the range of between about 0.1 to about 3 micron, and may particularly include radiation having a wavelength between about 0.75 micron to about 2.5 micron, or radiation having a wavelength between about 0.1 micron to about 1 micron.

It is preferred that the window absorb, reflect or scatter as little light as possible. The windows of the present invention are very thin, so that light will pass through most polymers, resins, and other materials suited for such windows, without excessive attenuation. Light is reflected at boundaries at which the index of refractance changes. Such light reflectance at each surface (both inner and outer surfaces) may be a major source of loss of light entering the window. Such losses due to reflectance at interface boundaries may be reduced or eliminated by using materials with indices of refraction similar to that of the material adjacent the interface. Thus, losses due to reflectance at the outer interface boundary may be reduced or eliminated by using materials with indices of refractance similar to that of the blood or plasma that will surround the window during use. For this reason, a window comprising a polymer or resin with an index of refraction between 1.3 to 1.4, preferably very near to 1.34, will have reduced or negligible losses due to reflectance at the outer window interface. Similarly, filling the space between the fiber-optic assembly and the inner face of the window (where the window's index of refraction is matched to blood or plasma) with saline or other solution with an index of refraction similar to blood or plasma, losses at the inner window surface would also be reduced.

Inventions embodying features of the invention include windows formed by the methods, and intracorporeal devices including windows formed by the methods. Such intracorporeal devices may include an imaging device, such as an imaging guidewire, an imaging catheter, an imaging endoscope, or other imaging device. In addition, inventions embodying features of the invention include combinations of objects and materials joined by the methods of the invention.

The novel methods disclosed herein avoid problems associated with conventional methods. Instead of press fitting an extruded window over formed guidewire ends to cause undesired expansion of the extruded window, the novel methods of the invention provide for deformation of a window preform softened by an increase in temperature, effective to form a window that is dimensioned within desired tolerances and without the need for excess window material that must be cleanly removed by some other operation. The methods of the present invention avoid problems of improper flow speed and of too-rapid cooling within the mold by the placement of the window preform in position within the mold before application of heat to soften it, so that no rapid flowing of melted plastic occurs, and there is no problem of cooling during flow of melted plastic.

Thus the present novel methods provide advantages over prior art techniques in overcoming these and other problems with conventional techniques.

DETAILED DESCRIPTION OF THE INVENTION

Figure 1A:
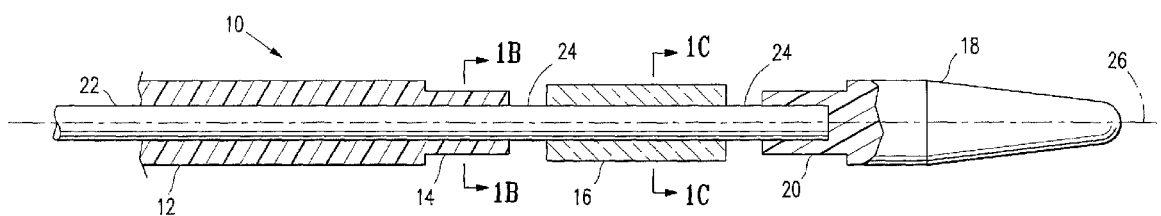
FIG. 1A is a longitudinal cross-sectional view of components of an imaging device embodying features of the invention, prior to insertion into a mold for manufacture of a window.
Figure 1B:
FIG. 1B is a transverse cross-sectional view of the guidewire components of FIG. 1A taken along line 1B—1B.
Figure 1C:
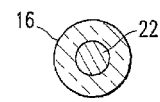
FIG. 1C is a transverse cross-sectional view of the guidewire components of FIG. 1A taken along line 1C—1C.

FIGS. 1A, 1B and 1C illustrate an assembly 10 embodying features of the invention comprising a proximal tubular member 12 with a distal section 14, a window preform 16, a distal member 18 with a proximal section 20, and a mandrel 22 with a distal section 24. As is illustrated in the longitudinal cross-section of the assembly shown in FIG. 1A, the assembly components are arranged substantially along longitudinal axis 26. Viewing components of the assembly 10 illustrated in FIG. 1A in order from left to right, mandrel 22 is disposed along longitudinal axis 26 and extends through and closely fits into the inner diameters of proximal tubular member 12, window preform 16 and distal member 18. Distal section 24 of mandrel 22 may be polished to a smooth surface finish in order to facilitate removal of mandrel 22 after formation of a window.

Proximal tubular member 12 is the guidewire component proximal to the window preform 16, with distal section 14 of the proximal tubular member 12 being adjacent window preform 16 and being configured to interface with the material of window preform 16 in a desired manner. Analogously, distal member 18 is the guidewire component distal to the window preform 16, distal member 18 containing a proximal section 20 that is adjacent to and configured to contact and interface with the material of window preform 16 in a desired manner. Distal member 18 may have a bore or depression configured to receive a mandrel 22, or may have a flat or curved face configured to contact a mandrel 22. In some embodiments of the invention, distal member 18 does not contact mandrel 22. In yet other embodiments, where the desire is to form a joint between a proximal tubular member 12 and a preform 16, there need be no distal member 18 at all. It will be understood that the pieces of the assembly, although tightly fitting, are slidably engaged and may be moved relative to one another. The pieces of the assembly may initially be in contact each other, although some or all the pieces of the assembly may initially not be in contact with other pieces of the assembly. With the application of force, proximal tubular member 12, window preform 16 and distal member 18 are able to move along mandrel 22 so as to decrease or increase the separation between window preform 16 and members 12 and 18. In FIG. 1, distal member 18 is shown with a depression configured to receive mandrel 22; it will be understood that in some embodiments of the invention, distal member 18 may have a bore configured to receive mandrel 22, or alternatively may comprise a flat face configured to contact window preform 16 and/or mandrel 22.

Distal section 14 of the proximal tubular member 12 and proximal section 20 of the distal member 18 comprise the window attachment areas. As illustrated in the Figures, the window attachment areas comprise portions of members 12 and 18 with reduced outer diameters, forming steps upon which material from window preform 16 may flow and attach. It will be understood that in some embodiments of the invention, one or both of window attachment areas 14 and 20 may include a portion or portions having increased inner diameter and unchanged outer diameter with respect to the remainder of members 12 and 18, forming ledges under which material from window preform 16 may flow and attach. The desired manner of interface with the material of window preform 16 is such that these sections provide a strong interface between the proximal tubular member and the window, and between the distal member and the window. Sections 14 and 20 may be roughened, grooved, provided with holes, provided with slots, provided with protrusions, treated or coated to improve adhesion of window materials, provided with an irregular surface, or in other ways known to those of ordinary skill in the art prepared and adapted to provide for a sturdy mechanical interface with the window. For example, treatments that may be applied to distal section 14 and proximal section 18 include application of a thin coating of Primacor™ (Dow Plastics, Midland Mich.), a thermoplastic adhesive, to improve the adhesion of nylon windows.

Figure 2A:
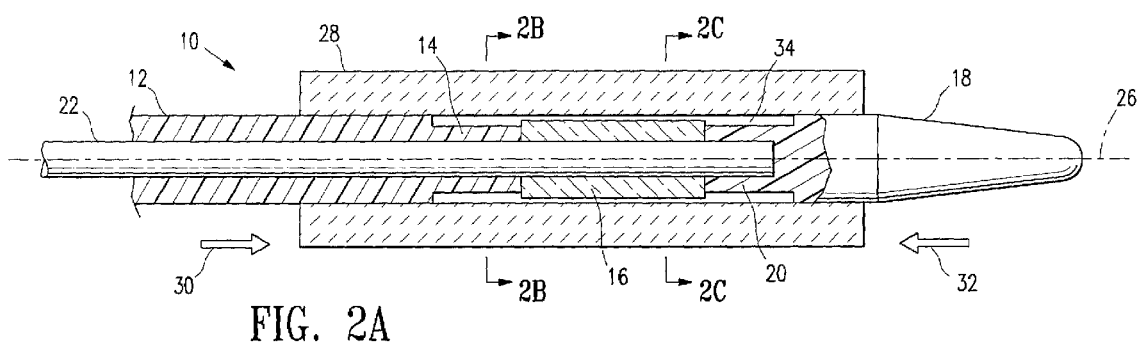
FIG. 2A is a longitudinal cross-sectional view of components of an imaging guidewire and mold embodying features of the invention at the start of the heat application step of a method of the invention.
Figure 2B:
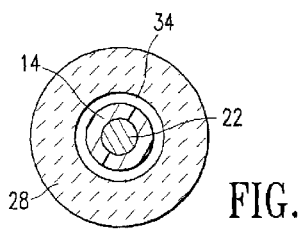
FIG. 2B is a transverse cross-sectional view of the imaging guidewire and mold components as illustrated in FIG. 2A, taken along line 2B—2B.
Figure 2C:
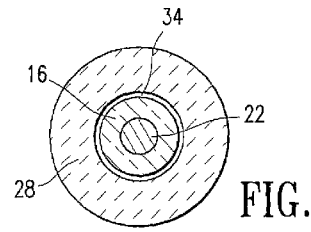
FIG. 2C is a transverse cross-sectional view of the imaging guidewire and mold components as illustrated in FIG. 2A, taken along line 2C—2C.

Referring now to FIGS. 2A, 2B and 2C, the assembly 10 illustrated in FIG. 1 is shown inserted into a mold 28 illustrating features of the invention. The mold 28 is shown in a cut away view in the longitudinal cross-section of the assembly shown in FIG. 2A. Preferably, mold 28 is configured to have a smooth circular inner diameter, especially in the region where the window will be formed. The inner diameter of mold 28 forms the outer diameter of the formed window. It is preferred that the outer diameter of the formed window be as smooth and dimensionally consistent as practical for optical reasons. The inner diameter of mold 28 is preferably sized to fit closely to portions of distal member 18 and proximal tubular member 12. Gap 34 within the mold 28 comprises those areas not blocked by mandrel 22, proximal tubular member 12, distal member 18, and distal and proximal sections 14 and 20. Gap 34 allows room for the flow of softened window material, and may optionally surround one or more of distal section 14, proximal section 20, and window preform 16.

The arrows 30 and 32 show the directions of forces applied to proximal tubular member 12 and distal member 18, respectively, during or after the time when the temperature of the window preform is raised, to urge proximal tubular member 12 and distal member 18 together, creating pressure in the softened material of window preform 16 effective to cause the window preform material to deform and to fill in gap 34 within the mold 28. Proximal tubular member 12 or distal member 18, or both, may move under the influence of the applied forces.

Mold 28 preferably has a smooth circular inner diameter and comprises a material having a higher melt temperature than the melt temperature of window material 16. Mold 28 may be made of metal, plastic, glass, ceramic, polymer, or combinations of materials.

Figure 3A:
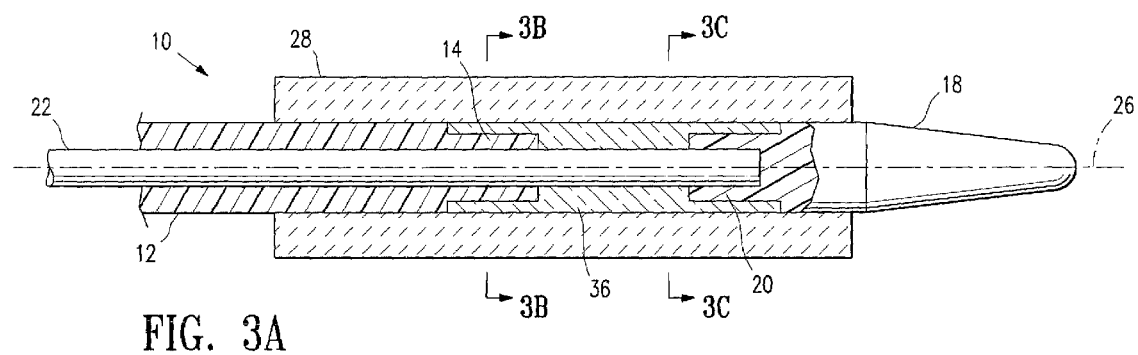
FIG. 3A is a longitudinal cross-sectional view of components of an imaging guidewire and mold embodying features of the invention after the heat application step of a method of the invention.
Figure 3B:
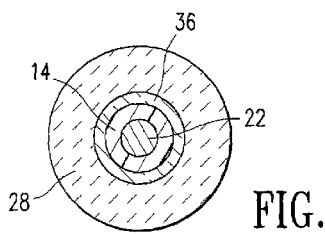
FIG. 3B is a transverse cross-sectional views of the guidewire and mold components as illustrated in FIG. 3A, taken along line 3B—3B.
Figure 3C:
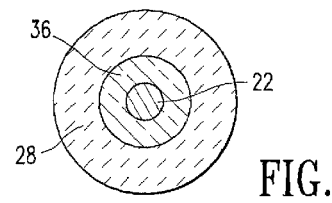
FIG. 3C is a transverse cross-sectional view of the guidewire and mold components as illustrated in FIG. 3A, taken along line 3C—3C.

The longitudinal cross-section of the assembly shown in FIG. 3A and the transverse cross-sections of the assembly shown in FIGS. 3B and 3C illustrate the assembly 10 and mold 28 after the temperature of the window preform has been raised, as by, for example, the application of heat, and the cooling of the mold 28. FIG. 3 illustrates a formed window 36, formed by the application of heat and force (as shown by arrows 30 and 32 in FIG. 2), after window preform 16 softened and/or melted, deformed (flowed) and then cooled. Note that gap 34 is not present at this step of the method, window material 16 having deformed so as to fill gap 34 and so to create the formed window 36 illustrated in FIG. 3. The size, shape and finish of the outer surface of formed window 36 is determined by the inner surface of mold 28; similarly, the size, shape and finish of the inner surface of formed window 36 is determined by the outer surface of mandrel 22. In the example illustrated in the Figures, proximal tubular member 12 is shown to have moved under the influence of force 30.

Figure 4A:
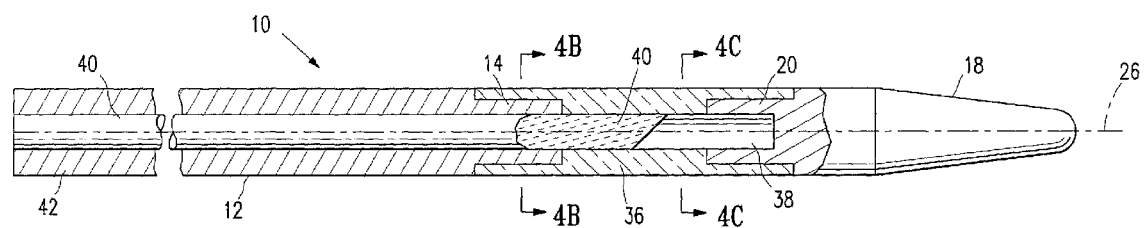
FIG. 4A, showing an optical imaging guidewire with a formed window, is a longitudinal cross-sectional view of an imaging guidewire embodying features of the invention following removal of the finished assembly from the mold and removal of the mandrel.
Figure 4B:
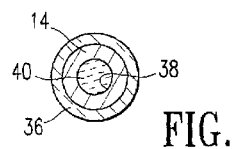
FIG. 4B is a transverse cross-sectional view of the optical imaging guidewire of FIG. 4A, taken along line 4B—4B.
Figure 4C:
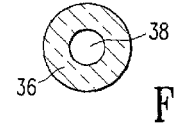
FIG. 4C is a transverse cross-sectional view of the optical imaging guidewire of FIG. 4A, taken along line 4C—4C.

FIGS. 4A, 4B and 4C illustrate the assembly 10 after it has been removed from the mold 28 and the mandrel 22 has been removed from the assembly 10. The outer surfaces of proximal tubular member 12, formed window 36, and distal member 18 form a smooth continuous surface suitable for a window for an intracorporeal imaging device such as a guidewire, catheter, or endoscope. The removal of the mandrel 22 provides a bore 38 extending through the interior of proximal tubular member 12, formed window 36 and at least partially into distal member 18 (illustrated in FIG. 4A as extending into proximal section 20 of distal member 18). A fiberoptic assembly 40 comprising an optical fiber and optical devices including a mirror and a lens, is illustrated located within bore 38 extending to the end 42 of the guidewire.

If the desired design configuration is the forming of a window alone, on one end and/or the other, as previously described, then proximal tubular member 12 and/or distal member 18 must be removed to complete the process.

It will be understood that proximal tubular member 12 may not be the entire proximal portion of the guidewire body. It may be only a section of it and/or only a component used to join the final window assembly proximally to the guidewire or guidewire assembly. Distal section 14 of proximal tubular member 12 may be configured to interface with the window material of window preform 16 in a desired manner. Where formation of the window alone is desired (for example, where it is not desired to join components to other proximal components), then the distal section 14 of proximal tubular member 12 may be configured to form the proximal end of the window in the desired configuration at the completion of the process. In such a case, distal section 14 may be designed or coated to release from the window material of window preform 16. Because mold release agents may interfere with the subsequent bonding and/or press fit of the window to a proximally mating section of the guidewire or guidewire assembly, distal section 14 is adapted for ease of release. In some embodiments of the method, in order to achieve this release of distal section 14 from window material of window preform 16, distal section 14 may be polished, permanently coated, tapered, or a combination of these. If the method is used for forming the window alone, or for joining a plastic part to another part without joining to other components, mandrel 22 and proximal tubular member 12 may be permanently joined or made in one piece. It will be understood that in the methods of joining a plastic part to a tubular member, the terms "window preform" and "window preform 16" may be used to denote the plastic part that is joined to the tubular member.

It will also be understood that distal member 18 may not be the entire distal portion of the guidewire. It may be only a section of it and/or only a component used to join the final window assembly distally to the guidewire or guidewire assembly. If it is not desired to join to other proximal components, that is, if forming of the window alone is desired, then the proximal section 20 of distal member 18 may be configured to form the distal end of the window in the desired configuration at the completion of the process. In this case, proximal section 20 is designed or coated to release from the window material. A method to achieve this release is to polish, permanently coat and/or taper proximal section 20 appropriately, which is preferred to the use of mold release agents, because mold release agents may interfere with the subsequent bonding and/or press fit of the window to the distally mating section of the guidewire or guidewire assembly. If forming the window alone, mandrel 22 and distal member 18 may be permanently joined or made in one piece, but only if mandrel 22 and proximal tubular member 12 are not permanently joined or made in one piece.

It will further be understood that distal section 14, or proximal section 20, or both, may assume various configurations and include features such as holes, grooves, channels, protrusions, and other features known in the art that may engage or interface with the window material of window preform 16 at the end of the process. Thus it will be understood that distal section 14, or proximal section 20, or both, may be configured so as to contact, engage, or grip window preform 16 or the formed window 36 (shown in FIGS. 3 and 4) in a manner that provides a mechanical lock to proximal tubular member 12 and distal member 18.

Mold 28 is made of a material with a higher melt temperature than the material comprising the window preform, and may comprise metal, plastic, glass, ceramic, polymer, or combinations of materials. A precisely dimensioned inner diameter of mold 28 may be formed by machining, including electronic discharge machining (EDM), polishing, molding, casting, or other methods. For example, a piece of glass tubing may be cast, blown, formed around a mandrel, or otherwise formed to have a precisely formed inner diameter, to create a mold 28 suitable for the practice of the method. In some embodiments of the methods of the invention, mold 28 is constructed from borosilicate glass tubing. Another method for forming a mold 28 is to place a piece of heat shrink tubing over a jig, such as a mandrel of the desired size adapted for manufacture of mold 28, and to shrink a length of its center over this jig. This jig is preferably precision ground and polished, so that the inner diameter of the shrunken portion of the heat shrink tubing will be very smooth and precisely dimensioned when the jig is removed. Removal of the jig may be effected simply by pulling it in a longitudinal direction out of the mold 28. Such removal may be aided by tapping the mold or jig before pulling the jig, or by brief application of heat. Alternatively, the mold 28 may be made in a clam shell configuration and opened to insert and/or remove the assembly 10 from the mold 28. However, it will be understood that such a configuration might result in a parting line being formed on the window which would interfere with light transmission.

Heat shrink tubing may be formed with a fluoropolymer (such as Teflon®, which is polytetrafluoroethylene, or PTFE), fluorinated ethylene propylene (FEP), or other materials. The diameter of heat shrink tubing is reduced by heating the tubing above a temperature, termed the shrink temperature, that is determined by the make-up and manufacture of the heat shrink tubing. It is preferred that where heat shrink tubing is used, the window preform material has a softening/melting temperature that is below the shrink temperature so as to avoid further shrinkage of the heat shrink tubing during formation of the window or joint.

Mold 28 is illustrated in FIG. 2A as having a single inner diameter dimension; however, it will be appreciated that if distal member 18 and proximal tubular member 12 have different outer diameters, then mold 28 may be formed to closely fit these outer diameters. In some embodiments where distal member 18 and proximal tubular member 12 have different outer diameters, mold 28 is formed to closely fit these outer diameters in the regions that border sections 20 and 14, respectively. In this case, the assembly 10 may only be inserted or removed from the larger inner diameter section of the mold 28 and the assembly 10's (or either proximal tubular member 12's or distal member 18's) position relative to the mold 28 must preferably be controlled so that the outer diameter of the window has the desired value. It will also be understood that the outer diameter of the formed window need not necessarily be as smooth as possible around the interface areas distal section 14 and proximal section 20, since these regions do not form an optical surface in the completed window.

To reduce possible loss of optical radiation or degradation of images passed through windows, smooth surfaces and matching of the index of refraction of the window with adjacent material (such as, e.g., blood or other body fluid) may be used. Complex strategies to match the indices of refractance may be employed to reduce losses due to reflectance at window boundaries. Such complex strategies include, but are not limited to, interposing between the fiber optic assembly and the window fluids (such as silicon oils) or coatings of a solid material having an index of refraction intermediate between the indices of refraction of the fiber optic assembly and the window, or intermediate to the index of refraction of the fiber optic assembly, the window and the external medium. Optionally, a coating of having a thickness of ¼ the wavelength (based on the center frequency of the light to be transmitted through the window) may be used to reduce losses due to reflectance.

In addition, window materials may further include additives, such as glass particles or fibers, as may be included to alter the strength, flexibility, or other properties of the window. Such additives may alter the optical properties of the window as well, by absorbing, reflecting, or refracting light passing through the window. It is preferred that any additives have a refractive index similar or identical to the refractive index of the window material, which is preferably similar to that of blood or plasma, in order to reduce any deleterious optical effects of the additives. Where such additives are included, it is preferred that the size, number, and concentrations of such additives be controlled in order that any light scattering, light refraction, light absorption, or light reflection that may result from the additives be limited to acceptable levels.

The window preform may include a material or a combination of materials that soften as the temperature is raised. The window preform may be made with any suitable material which may deform under the desired conditions, including suitable plastic or resinous materials. Plastics that soften as their temperature is raised, including polymeric materials or polymer blends, are suitable materials for window preforms of the invention. Alternatively, window preforms may include resins, including epoxy resins, that have been cooled or frozen, and soften or melt as the temperature of the cooled or frozen preform is raised as it warms to ambient temperature. In addition, window preforms may include materials that change their physical properties or change state in response to light, such as a resin or resin system that responds to ultraviolet, visible, or infra red light. Under a variety of conditions, such as heating, mixing, or under exposure to light, resins or resin systems "cure" (become polymerized). Window preforms comprising resins are preferably uncured (not substantially polymerized) or partially uncured (incompletely polymerized); thus, in preferred embodiments of window preforms comprising resins, the resins are at least partially uncured.

In some embodiments of the invention, the plastic preform may comprise a combination of plastic materials, a resin that is at least partially uncured, a combination of resins at least some of which are at least partially uncured, and other materials and combinations of materials. Thus, the window preform may include a material selected from the group consisting of acrylic, polycarbonate, nylon, Teflon®, polyethylene terephthalate (PET), tensilized PET, resins, and blends thereof. Resins used in a window preform may be at least partially uncured. Preferred window materials have high moduli of elasticity. Although materials such as glass, fused silica and $MgF_2$ can be stronger and have higher flexural moduli than plastics, they are brittle and shatter when they fail. Such a failure mechanism is not tolerable in a guidewire or other device for use within a body lumen. Plastics can deform more without generating failure forces and their failure mechanism is to permanently deform, often significantly, prior to breaking, making them more suitable for use in devices for accessing body lumens than more brittle materials.

In some embodiments of the method, mold 28 is heated effective to achieve a temperature hot enough to soften (which may include melting) the window preform 16, but not hot enough to degrade or burn the window material. For example, mold 28 may be heated sufficiently to soften the window material 16 effective to allow window material 16 to deform as desired, e.g., when under pressure. As used herein, "deform" means to alter the shape of an object by pressure, stress, or heat, and "deformation" is the alteration of the shape of an object by pressure, stress, or heat. Deformation may include flow, as of an object that has melted.

Softening or melting that is effective to allow window material 16 to deform may be due to a change in viscosity of the material, or may be due to a phase change in the material. Some plastic materials, including some materials of which window preform 16 is preferably comprised, have a material conversion temperature at which the state of the material shifts from amorphous to liquid. In addition, some materials, such as light-sensitive resins and resin systems, may be induced to change state between amorphous and liquid states by exposure to light or other radiation. The mechanical properties of a material may be altered during a change in viscosity or a phase change. In particular, during a change in viscosity or a phase change from amorphous to liquid, the flow of a plastic material may not be controlled. In order to avoid potential problems presented by these situations, in some embodiments of the methods, the temperature is controlled during the molding process so that the material conversion temperature of the material of window preform 16 is not exceeded. In addition, in some embodiments of the methods, exposure to radiation is controlled during the molding process to control the mechanical and physical properties of the material of window preform 16.

In some embodiments of the method, the window preform includes a frozen resin, such as a frozen epoxy resin mixture, that melts and softens within the mold as it returns to ambient temperature. In such embodiments of the method, no external heat is required to effect the softening of the window preform. In addition, some resins and resin systems are light-sensitive, so that the physical properties or physical state of the resins and resin systems change upon illumination by light. Window preforms including such resins or resin systems may be placed within a translucent or transparent mold to form mold assemblies that allow the resins to receive appropriate wavelengths of light. Such mold assemblies may be used in the methods and systems of the invention to form windows or joints using light instead of, or in conjunction with, heat, to effect the softening of the window preform. In some embodiments, the resins or resins systems may harden upon illumination.

In some embodiments of the method, heating is performed whereby the temperature is controlled to effect the desired deformation without damage to window preform 16 and without adversely affecting its optical and mechanical properties. The heat or heating energy used to soften or melt the window preform 16 may be applied any number of ways, including but not limited to induction heating, conduction heating, infra-red heating, hot air heating, ultrasonic heating, friction heating, and other heating methods known to those of ordinary skill in the art. In some embodiments of the methods, temperature controlled hot air (i.e. convection heating) is applied as a method of heating the window preform. The temperature of hot air used for hot air heating may be in a range of between about 200° F. and about 800° F., preferably in a range of between about 300° F. to about 500° F.

The methods of the present invention allow for the continuous control of temperature and force (e.g., forces 30 and 32 illustrated in FIG. 2A) during formation of the window, and so allow for the continuous control of the movement of proximal tubular member 12 and distal member 18. This provides the advantage that the window preform 16 may be caused to flow slowly and then to cool slowly at much lower pressures (or sequences of pressures) than are required for other molding processes. In this way, with the present invention, there can be considerably lower internal stresses in the window and in its attachments than are provided by other molding processes. These lower internal stresses make the polymer window stronger, and make its attachments to the proximal tubular member 12 and distal member 18 stronger. The lower pressures of the molding process are also desirable because they help to prevent undesired loss of material ("flash"), by allowing for the control or elimination of material flow into gaps between the mandrel and proximal tubular member 12 and distal member 18 or between the mold and proximal tubular member 12 and distal member 18.

It will be understood by those of ordinary skill in the art that any supporting structures used to hold the components of assembly 10 and to apply forces 30 and 32 to the components must allow for relative movement between proximal tubular member 12 and distal member 18 under the application of these forces. However, it will be understood that in some embodiments of the methods, one, or both tubular members 12 and 18 may move substantially under the influence of the forces illustrated by arrows 30 and 32.

In some embodiments of the invention, window preform 16 is a piece of an extruded tube of the desired window material, with its outer diameter the same or just less than the ultimate outer diameter of the completed window to be formed by the process. In other embodiments, the inner diameter of window preform 16 is slightly greater than the outer diameter of the distal section 24 of mandrel 22 so as to allow insertion of at least a portion of the mandrel 22 into the window preform 16. The volume of window preform 16 is preferably chosen to be the desired volume of the desired final window material configuration. It will be understood that, where window preform 16 comprises a tube of substantially constant wall thickness, the volume of window preform 16 is substantially determined by the length of window preform 16. If the process produces flash, that is, if window material may be lost during the process, as may occur, for example, by flow of window material into undesired gaps between the assembled components, then additional window material may be provided, as by increasing the length of window preform 16 to compensate for material expected to be lost.

In order to avoid the formation of bubbles in the windows, materials containing volatile additives and materials that degrade during heating are not used, or used only sparingly, in window preforms. Where materials presenting risk of bubble formation are used, bubbles may be avoided by preferentially heating one end of the preform during window formation, to cause plastic flow in the window preform so that bubbles or voids do not form. Any air present that may be present in any small gaps while putting the assembly together prior to heating will be pushed out by the flow wave front.

The window preform may have any suitable length, for example a length of between about 1 mm and about 11 mm. In some embodiments of the methods of forming a window, the window preform has a length of between about 2 mm and about 6 mm, preferably between about 3 mm and about 5 mm. Windows formed by the methods of the invention may have any suitable length, for example, a window formed by the methods of the invention may have a length of between about 0.3 mm and about 10 mm. In some embodiments, a window may have a length of between about 1 mm and about 5 mm, preferably between about 2 mm and about 4 mm.

Windows formed by the methods of the invention may be of any suitable size, for example windows formed by the methods may comprise annuli with an inner diameter of between about 0.001 inches and about 0.02 inches and an outside diameter of between about 0.005 inches and about 0.05 inches. In some embodiments of the methods, windows formed by the methods comprise annuli with an inner diameter of about 0.0075 inches or smaller and an outside diameter of about 0.014 inches or smaller.

It will be appreciated that the greater the cross-sectional area of the window the stronger the window area. Maximum strength is desired for safety reasons. In addition, mandrels are routinely precision ground to tolerances of +/−0.0002" or less. Thus the inner diameter of a mold 28 (which defines the outer diameter of window 36) and the outer diameter of a mandrel 22 (which defines the inner diameter of window 36) can be tightly controlled to provide desired dimensions within tight tolerances. Thus an advantage of the present methods is that they provide windows of greater cross-sectional area within desired smoothness and dimensional tolerances.

Fiber optic assembly 40 may comprise any assembly or system suitable for use in an imaging system, and may comprise components and devices for imaging in the optical, infra-red, or any suitable wavelength. Imaging may be by means of scanning, including confocal means, or other imaging methods known in the art. It will be understood that guidewire end 42 may comprise any guidewire end suitable for an intracorporeal device, and preferably comprises an optical interface effective to transmit optical signals carried by fiber optic assembly 42.

The methods of the present invention solve the problems of bonding, maintenance of tolerances, high cost, and low probability of success associated with prior methods. Mandrels, glass molds, heat shrink tubing (such as FEP, PTFE and other polymers, which may be used, e.g., to form molds in some embodiments of the invention) and hot air sources are relatively inexpensive. Because the window material 16 surrounds the inner diameter-forming mandrel 22 during the melting and deforming step or steps, all forces on the mandrel 22 will be nearly in balance at all times. Any imbalance in the forces would be of such a low level that only a slight momentary bending could occur, which would not cause a permanent deformation of the mandrel 22. In some embodiments of the invention, the plastic remains melted in the mold 28 for longer than in a conventional mold, so that even if there were to be some slight deformation of the mandrel 22, the mandrel 22 would recover its straightness before cooling.

Where the methods of the invention are used to form a guidewire in which the optical assembly (comprising an optical fiber) is not required to move within the window, the optical assembly may itself be used as the mandrel, and be encapsulated within the window. In this case, there is no need to remove the mandrel at the end of the process. In this case as well, it is preferred that the optical assembly not engage the distal member so as to avoid damaging it mechanically or to avoid blocking the light transmitting portions of the window. An interface is eliminated by encapsulating the optical assembly within the window in this way, reducing the interfaces at which indices of refraction need be matched.

It will be understood that methods of forming windows that are variants of the methods described above are also within the scope of the invention. For example, in some embodiments of the invention proximal tubular member 12 and/or a distal member 18 may have end sections which form recesses with reduced inner diameter and the same outer diameter as member 12 and/or 18, instead of forming steps with reduced outer diameters as shown in FIGS. 1–4. In such case, it will be understood that window preform 16 may adhere to a proximal tubular member 12 and/or a distal member 18 by flowing into a recess in these members that is adapted to receive the window material, instead of flowing onto the step portion to fill out the outer diameter as illustrated in FIGS. 1–4. In addition, methods and devices of the invention are further illustrated and explained in the Examples.

Where the methods of the invention are used to form a joint between two objects or materials, corresponding to a proximal tubular member and to a preform as illustrated in FIG. 1, there need be no member corresponding to distal member. For example, a plastic part may be joined with a tubular member by a method including the steps of placing an assembly at least partially within a mold, where the assembly includes a tubular member, a plastic preform comprising a material that softens when heated, and a mandrel; softening the plastic preform (e.g., by heating); and applying force effective to urge the tubular member and the plastic preform together, effective to deform the plastic preform and to join it to the tubular member. The plastic preform may comprise a material selected from the group consisting of acrylic, polycarbonate, nylon, Teflon® (polytetrafluorethylene), polyethylene terephthalate (PET), tensilized PET, resins, and blends thereof. Thus, the plastic preform may comprise a combination of plastic materials, a resin that is at least partially uncured, a combination of resins at least some of which are at least partially uncured, and other materials and combinations of materials. The tubular member may be made of materials including a metal, a ceramic, or other materials.

In the methods of joining a plastic part with a tubular member, the plastic preform may deform during softening or after it has been softened, and the step of applying force may occur during or following the softening of the plastic preform. In some embodiments of the methods, the assembly may be cooled. In some embodiments of the methods, the assembly may be removed from the mold; the removal of the assembly may include a step including providing heat. In yet other embodiments, the methods include removing the mandrel from the assembly; the removal of the mandrel from the assembly may include a step including providing heat.

EXAMPLE 1

A borosilicate glass mold is prepared with a smooth circular inner diameter of 0.014 inches.

A mandrel with an outer diameter of 0.0075 inches and a smoothly polished end is placed through a hypotube guidewire body so that it protrudes from both ends of the hypotube guidewire body. The outer diameter of the mandrel is sized to be the largest possible to allow free movement within the hypotube guidewire body. A piece of window tubing is placed over the end of the mandrel and moved up against the end of the hypotube guidewire body. The volume of the window tubing is at least the volume of the desired final window and window material parts. The outer diameter of the window material is just less than 0.014" (as large as possible while still less than the inner diameter of the mold).

The proximal end of the tip of the guidewire assembly is fitted over the protruding end of the mandrel, and pushed towards the hypotube guidewire body so that the window material is between and touching both the hypotube guidewire body and the proximal end of the tip of the guidewire assembly. The mold is slipped over these assembled parts, and the window material is centered inside the mold. While force is applied to both ends of the window material by urging the hypotube guidewire body and the tip of the guidewire assembly towards the window material between them, heat is applied to the mold effective to produce a temperature sufficient to melt the window material but not the mold.

After allowing sufficient time for the window material to deform and to flow over the mechanical lock portions of the hypotube guidewire body and the tip of the guidewire assembly (the lock portions are illustrated in the figures as distal section 14 of proximal tubular member 12 and proximal section 20 of distal member 12), the heat is removed and the assembly is allowed to cool. The assembly is removed from the mold, and then the mandrel is removed from the assembly. A quick, brief re-exposure to heat may be desired to facilitate removal of the assembly from the mold or of the mandrel. After removal from the mold and removal of the mandrel, the formation of the window is complete.

EXAMPLE 2

Window assemblies have been produced with the following items, where item numbers relate to similar components illustrated in the Figures. Item 22 is a mandrel and item 12, a hypotube, is a proximal tubular member. A hypotube is a tubular element useful in the manufacture of a guidewire, for example. Item 14 is a distal section of a proximal tubular member, that is, in this example, a distal portion of the hypotube. Item 16, a window preform, is an imaging window. Item 20, the proximal section of a distal member, is a proximal portion of a guidewire tip. Item 18, a distal member, is a guidewire tip. Item 28, a mold, is a mold formed from borosilicate glass tubing. Item 40, a fiberoptic assembly 40, as illustrated in FIG. 4 above, fits within bore 38 left by removal of mandrel 22. The following abbreviations are used below: "OD" for outer diameter; "ID" for inner diameter; "NiTi" for nickel titanium alloy, or nitinol; "PET" for polyethylene terephthalate; "SS" for stainless steel; "DFT" for bis (p-fluorophenyl)-2,2,2 trichloroethane; "VSS" for vanadium stainless steel; and "GRIN" for graded index of refraction. As used in the Table below, "BMW design," "S' port design," and "Balance design" refer to intravascular guidewires that are commercially available from Advanced Cardiovascular Systems (Santa Clara, Calif.).

| Item # | Description | Material and Dimensional Information |
|---|---|---|
| 22 | Mandrel | Teflon ® Coated Mandrel |
| | | Parylene Coated Mandrel |
| | | (Approximate Dimensions: OD: 0075") |
| 12 | Hypotube | NiTi/Chromium Doped Hypotube |
| | | Approximate Dimensions |
| | | |
| | | Overall Length: 40 cm |
| | | OD: .0135" |
| | | ID: .0075 |
| 14 | Distal Portion of Hypotube (Note: | NiTi/Chromium Doped Hypotube Approximate Dimensions |
| | This was manufactured by plunge grinding the material) | OD: .0104" Length: 7 mm |
| 16 | Imaging Window | Acrylic |
| | | Polycarbonate |
| | | Nylon |
| | | Tensilized PET |
| | | Approximate Dimensions |
| | | |
| | | OD (i.e. profile) for all sections: .0135" |
| | | Section bonded to Item 3: [Length: 4 mm] [ID: .0104"] |
| | | Center Section: [ID: .0066] [Length: 3 mm] |
| | | Section bonded to Item 5: [Length: 4 mm] [ID: .0081"] |
| 20 | Proximal portion of Guidewire tip | Approximate Dimensions Max. OD of core wire: .0080" |
| 18 | Guidewire Tip | Materials Used |
| | | |
| | | NiTi/SS DFT |
| | | 304 VSS |
| | | NiTi |
| | | Approximate Dimensions |
| | | |
| | | Max. OD of core wire: .0080" |
| | | Possible Designs |
| | | |
| | | 5 cm long BMW core-to-tip design |
| | | 7 cm long BMW design |
| | | 5 cm long core-to-tip S'port design |
| | | 7 cm long S'port design |
| | | 5 cm long Balance design |
| | | 7 cm long Balance design |
| 28 | Glass Tubing | Material: Borosilicate |
| | | OD: .070" |
| | | ID: .0139" |
| | | Length: 2" |
| 40 | Fiberoptic Assembly | Fiberoptic cable with thin polyimide jacket (Single mode Fiber) with GRIN lens and Prisms/Mirror attached. |
| | | Approximate Dimensions |
| | | |
| | | Core OD: 8 microns |
| | | Cladding OD: 125 microns |
| | | Polyimide Jacket |
| | | OD: 140 microns |
| | | Maximum OD: .055" |

EXAMPLE 3

Windows comprising tensilized PET and polycarbonate were formed by the method of this example. Window preforms were cut to length (1–10 mm) from tubes of tensilized PET and of polycarbonate. A drill was used to create a concave taper on both ends of the window preform. This taper helps to center the proximal tubular member and the distal member. Where only one of the proximal tubular member and the distal member were to be attached, only one end of the window preform need be drilled to form a taper. A NiTi/Chromium Doped hypotube was used for the proximal tubular member. The proximal tubular member was next inserted into and clamped in a motorized collet. The proximal tubular member was then rotated in the collet and diameter of the end of the proximal tubular member was reduced using a grinding stone to form a distal section suitable for receiving the window preform. Next, a mandrel was inserted into the bore of the proximal tubular member, leaving sufficient length sticking out of the proximal tubular member to support the inner diameter of the window preform during assembly. A borosilicate glass tube mold was then slid over the window preform. Under inspection with a microscope to control the process, and with the proximal tubular member spinning, the mold and the window preform were pressed into the spinning proximal tubular member. Alternatively, in cases where the mold is opaque, the increase in force required to produce lateral motion of the window preform or proximal tubular member may be monitored to control the process. The friction from this process, including the spinning of the proximal tubular member and the pressure on the mold and window preform as they were pressed into the proximal tubular member, was sufficient to soften tensilized PET and of polycarbonate window preforms for the formation of windows by this method. Following this last step, the assembly was removed from the collet. In order to attach a distal member to the distal end of the window, the distal member may be inserted into the collet and rotated, and the piece formed by these steps may be turned around, with the mold around the window, including the distal end of the window, so that the distal end of the window may be pressed into the distal member.

EXAMPLE 4

This example illustrates the formation of a joint between a plastic preform (termed a window preform in preceding examples) and a hypotube according to a method of the invention. A borosilicate glass mold is prepared with a smooth circular inner diameter of 0.014 inches. The mold is configured to hold a hypotube and a plastic preform within its bore.

A mandrel with an outer diameter of 0.0075 inches and a smoothly polished end is placed through a nickel titanium chromium-doped hypotube guidewire body so that it protrudes from both the proximal and distal ends of the hypotube guidewire body. The outer diameter of the mandrel is sized to be the largest possible to allow free movement within the hypotube guidewire body. A plastic preform comprising a tubular piece of plastic to be joined to an end of the hypotube is placed over the end of the mandrel and moved up against the distal end of the hypotube guidewire body. It will be understood that the plastic preform could also be a cylindrical piece of plastic placed in contact with the mandrel. The outer diameter of the plastic preform material is just less than 0.014" (as large as possible while still less than the inner diameter of the mold). The plastic preform comprises PET, although other plastic materials are also suitable.

The plastic preform is pushed towards the hypotube guidewire body so that the plastic preform material is touching the hypotube guidewire body. The mold is slipped over these assembled parts. While force is applied to both ends of the plastic preform material by urging the hypotube guidewire body and the plastic preform material together, heat is applied to the attachment side of the mold effective to produce a temperature sufficient to melt the plastic perform material but not the mold. Such application of heat to the attachment side of the mold is effective to reduce or prevent the application of heat to the distal end of the plastic preform opposite to the site of attachment to the hypotube. Alternatively, a distal portion of the plastic preform could be shielded from the heat.

After allowing sufficient time for the plastic preform material to deform and to flow over the mechanical lock portions of the hypotube guidewire body (lock portions are illustrated in the figures as distal section 14 of proximal tubular member 12), the heat is removed and the assembly is allowed to cool. The assembly is removed from the mold, and then the mandrel is removed from the assembly. A quick, brief re-exposure to heat may be desired to facilitate removal of the assembly from the mold or of the mandrel. After removal from the mold and removal of the mandrel, the joining of the plastic perform and the hypotube is complete. In this way a joint is formed between the plastic preform and the hypotube. It will be understood that these methods are suitable for joining many different materials.

While particular forms of the invention have been illustrated and described, it will be apparent that various modifications can be made without departing from the spirit and scope of the invention. Accordingly, it is not intended that the invention be limited except as by the appended claims.

What is claimed is:

1. A method for forming a substantially cylindrical window for an intracorporeal device, comprising:
    placing at least partially within a mold an assembly with a longitudinal axis, said assembly comprising a proximal tubular member, a distal member, a window preform comprising a material that may soften, said window preform being disposed between said proximal tubular member and said distal member, and a mandrel disposed along said longitudinal axis at least partially within said proximal tubular member, said window preform, and said distal member;
    softening said window preform; and applying force effective to urge together said proximal tubular member and said distal member effective to deform said window preform to form a window.

2. The method of claim 1, wherein said step of softening the window perform comprises heating the window preform.

3. The method of claim 1, wherein said applying force step occurs during or following said step of softening the window preform.

4. The method of claim 2, further comprising cooling the assembly.

5. The method of claim 4, further comprising removing the assembly from the mold.

6. The method of claim 5, wherein the step of removing the assembly from the mold further comprises heating.

7. The method of claim 5, further comprising removing the mandrel from the assembly.

8. The method of claim 7, wherein the step of removing the mandrel further comprises heating.

9. The method of claim 1, wherein the window preform comprises a polymeric material.

10. The method of claim 1, wherein the window preform comprises a combination of polymeric materials.

11. The method of claim 1, wherein the window preform comprises a resin that is at least partially uncured.

12. The method of claim 1, wherein the window preform comprises a combination of resins at least some of which are at least partially uncured.

13. The method of claim 1, where the window preform comprises a material selected from the group consisting of acrylic, polycarbonate, nylon, polytetrafluoroethylene (Teflon®), polyethylene terephthalate (PET), tensilized PET, resins, and blends thereof.

14. The method of claim 1, wherein the window preform has a length of between about 1 mm and about 11 mm.

15. The method of claim 2, wherein the step of heating the window preform is effected by at least one method selected from the group consisting of induction heating, conduction heating, infra-red radiation, ultrasonic heating, friction heating, hot air heating and allowing the temperature of the window preform to rise to ambient temperature.

16. The method of claim 15, wherein the step of heating the window perform comprises hot air heating.

17. The method of claim 16, wherein the temperature of hot air used for hot air heating is between about 300° F. and about 500° F.

18. The method of claim 1, wherein the mandrel has a distal end, and wherein said distal end is polished.

19. The method of claim 1, wherein the mold comprises a material selected from the group consisting of metal, glass, plastic, ceramic, polymer, and combinations thereof.

20. A method for forming a substantially annular window for an intracorporeal device, comprising:

placing at least partially within a translucent mold an assembly with a longitudinal axis, said assembly comprising a proximal tubular member, a distal member, a window preform comprising a material that softens when illuminated, said window preform being disposed between said proximal tubular member and said distal member, and a mandrel disposed along said longitudinal axis at least partially within said proximal tubular member, said window preform, and said distal member;

illuminating the window preform effective to soften said window preform disposed between said proximal tubular member and said distal member; and applying force effective to urge together said proximal tubular member and said distal member effective to deform said window preform to form a window.

21. The method of claim 20, wherein said illumination comprises illumination selected from the group consisting of illumination with ultraviolet light, illumination with visible light, and illumination with infrared light.

* * * * *